(12) United States Patent  
Stanton et al.

(10) Patent No.: US 7,933,007 B2  
(45) Date of Patent: Apr. 26, 2011

(54) METHOD AND APPARATUS FOR POSITION OPTIMIZATION OF A FIELD GENERATOR

(75) Inventors: Douglas Stanton, Ossining, NY (US); Jochen Kruecker, Washington, DC (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 396 days.

(21) Appl. No.: 12/095,510

(22) PCT Filed: Dec. 8, 2006

(86) PCT No.: PCT/IB2006/054718  
§ 371 (c)(1),  
(2), (4) Date: May 30, 2008

(87) PCT Pub. No.: WO2007/069170  
PCT Pub. Date: Jun. 21, 2007

(65) Prior Publication Data  
US 2010/0177296 A1    Jul. 15, 2010

Related U.S. Application Data

(60) Provisional application No. 60/750,753, filed on Dec. 15, 2005.

(51) Int. Cl.  
*G01P 3/36* (2006.01)
(52) U.S. Cl. .......... 356/139.01; 356/139.02; 356/139.03
(58) Field of Classification Search ........ 356/3.01–3.15, 356/4.01–4.1, 5.01–5.15, 6–22, 28, 28.5, 356/139.01–139.1  
See application file for complete search history.

(56) References Cited

U.S. PATENT DOCUMENTS

| 5,886,775 | A | * | 3/1999 | Houser et al. ............... 356/4.01 |
| 5,891,158 | A | * | 4/1999 | Manwaring et al. ......... 606/130 |
| 6,366,799 | B1 | * | 4/2002 | Acker et al. ................. 600/424 |

FOREIGN PATENT DOCUMENTS

| WO | WO9729683 | 8/1997 |
| WO | WO9729685 | 8/1997 |

* cited by examiner

*Primary Examiner* — Thomas H Tarcza  
*Assistant Examiner* — Luke D Ratcliffe

(57) ABSTRACT

An electro-magnetic tracking system includes a system controller having a sensor interface, a generator, and a positioning and angular orientation configuration. The generator is responsive to the system controller for generating an electromagnetic field that includes a tracking volume of highest accuracy. The highest accuracy corresponds to an accuracy of the sensor interface and system controller to detect a sensor physically located within the tracking volume versus a lesser accuracy of the sensor interface and system controller to detect the sensor if the sensor is located outside of the tracking volume. The positioning and angular orientation configuration is coupled to the field generator for visibly optimizing (i) a positioning and/or (ii) an angular orientation of the electromagnetic field generator such that the tracking volume lies within a centroid of a physical volume of interest, thereby enabling a detection of a sensor within the tracking volume with a highest accuracy.

24 Claims, 5 Drawing Sheets

METHOD AND APPARATUS FOR POSITION OPTIMIZATION OF A FIELD GENERATOR

CROSS REFERENCE TO RELATED APPLICATIONS

This application claims the benefit of International Application Number PCT/IB2006/054718, filed Dec. 8, 2006, and U.S. Provisional Application Ser. No. 60/750,753 filed Dec. 15, 2005 which are incorporated herein in whole by reference.

The present embodiments relate generally to medical systems and more particularly, to a method and apparatus for position optimization of a field generator.

Electro-magnetic tracking systems generally consist of a field generator, one or several small sensor coils, and signal processing hardware and software. The field generator contains a number of transmitter coils which radiate an electro-magnetic field through a tracking volume. When used in medical applications, the sensor coils are placed inside a medical device, such as a needle or catheter, and moved through a volume of interest. So long as the tracking volume and the volume of interest substantially coincide, the information regarding the position of the tracked medical device is ascertained and processed, for example, using the signal processing hardware and software. One example of an electro-magnetic tracking system is the Aurora, which is commercially available from NDI, of Waterloo, Ontario, Canada.

However, electro-magnetic tracking systems have limits on the volume that can be examined accurately (i.e., the tracking volume). FIG. 1 is a diagram view of an electro-magnetic tracking system 10 as discussed herein above. The electro-magnetic tracking system 10 includes an electro-magnetic field generator 12 which generates electro-magnetic waves directed into a tracking volume. A preferred tracking volume that is characterized as having the highest accuracy is called the "sweet spot" of the electro-magnetic tracking system, indicated by reference numeral 14. A sensor coil 16 is illustrated as occurring within the sweet spot 14. The "ideal placement" of the electro-magnetic field generator is such that the sweet spot 14 lies in the centroid of the physical area to be probed with the tracked medical device or devices. The "ideal placement" may also be affected by the environment, in particular by any objects interfering with the electro-magnetic field of the tracking system.

While usually great care is taken to control the positioning of a medical device in an operative procedure, no such care is typically taken with respect to positioning of a field generator. Field generators typically have no reference planes or points. The generator is positioned manually, close to the physical area of interest, but otherwise arbitrarily (i.e., with respect to an exact position and/or orientation). Therefore, placement of the field generator may differ from an ideal placement in both position and orientation, which can adversely affect the accuracy of the electro-magnetic tracking system significantly.

In addition, the simple manual placement of the field generator makes it extremely difficult to accurately repeat the positioning of the generator. Thus, if the generator was moved accidentally during an experiment, or if an experiment is to be repeated after moving the generator, the tracking data after repositioning may not be directly comparable to the tracking data before repositioning. As a result, it may be necessary to recalibrate the electro-magnetic tracking system or the corresponding data sets.

For registration of an electro-magnetic tracking space with an imaging space, current practice is to produce a data set created by placing the field generator above the patient. In a typical case, the current practice also includes placing a tracked pointer probe at fiducial markers on a patient's skin. The fiducial markers are also identified in image data sets for probe calibration and registration to other imaging modalities. Although the fiducial markers are used as a reference, there is no guarantee that the markers fall within the "sweet spot" of the electro-magnetic field tracing system instrument.

In addition, distortions to the electro-magnetic field can be caused by adjacent medical equipment, thus exacerbating the alignment problem. If such distortions are accounted for in software and the system (i.e., field generator) alignment is changed, a means must exist to accurately and quickly reposition the components, or otherwise the distortion must be remapped in the software.

Accordingly, the maintenance of a constant and well-defined spatial relationship between the field generator and the physical area of interest is desired. An improved method and system for overcoming the problems in the art is also desired.

Figure 5:
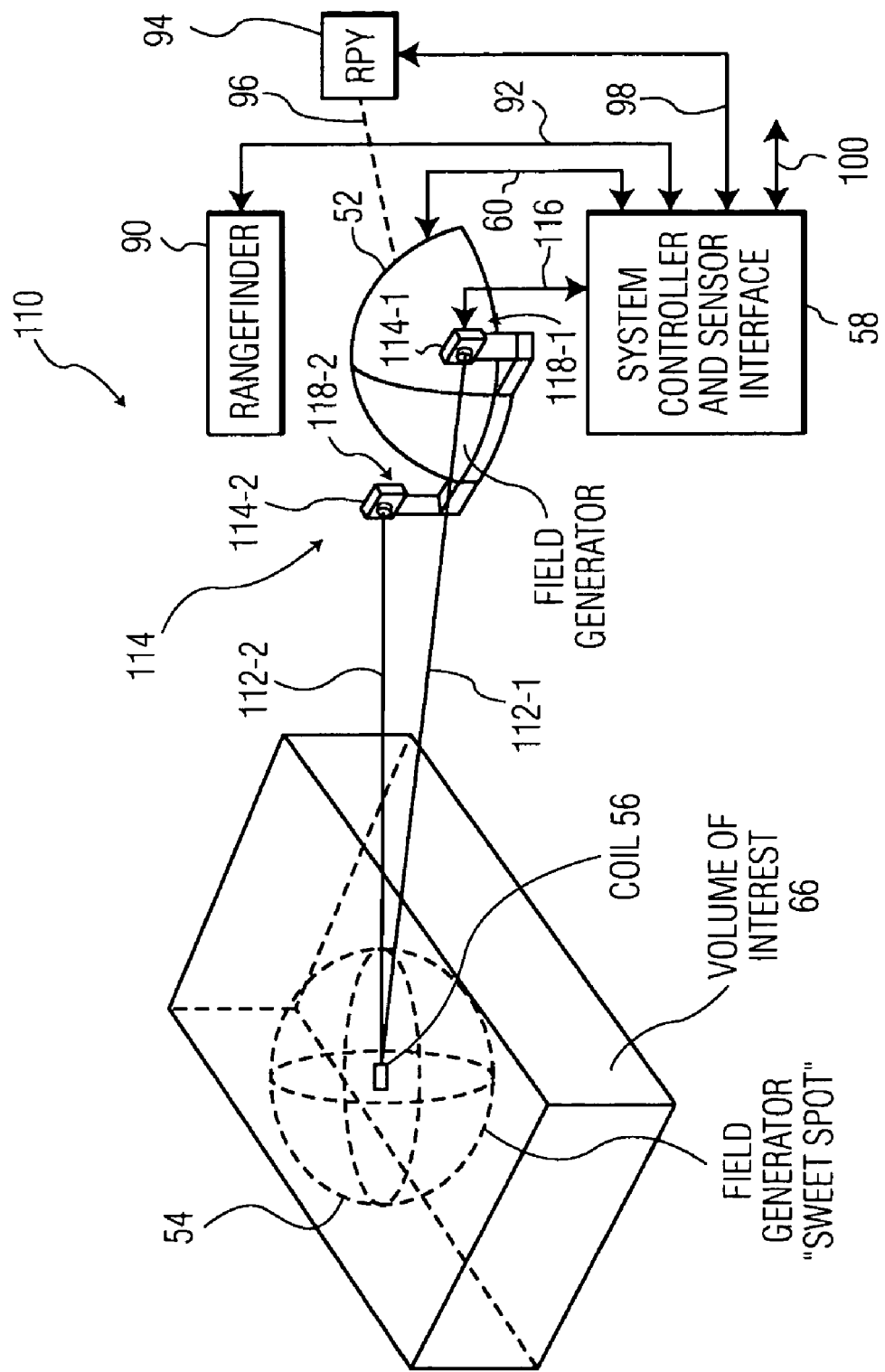
Figure 6:
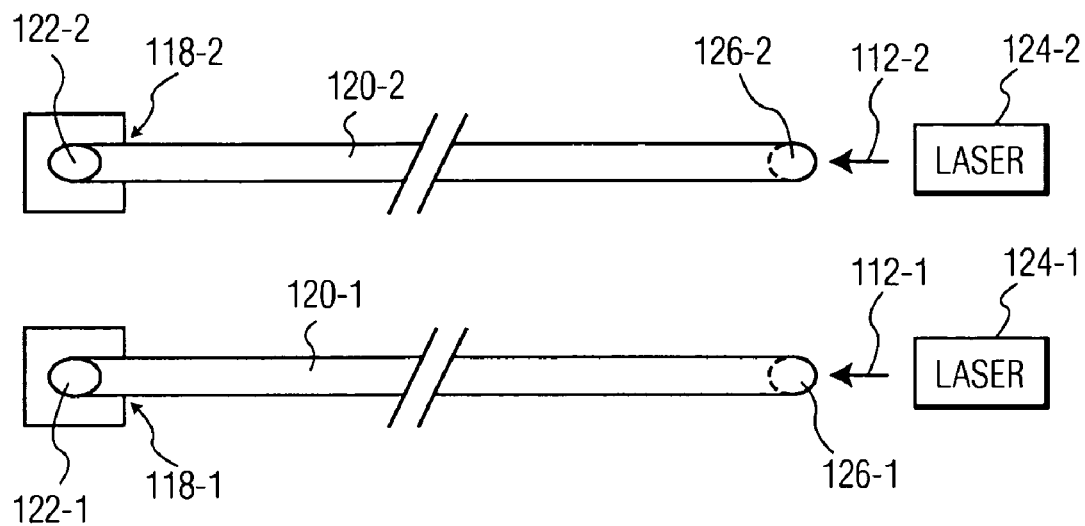
Figure 7:
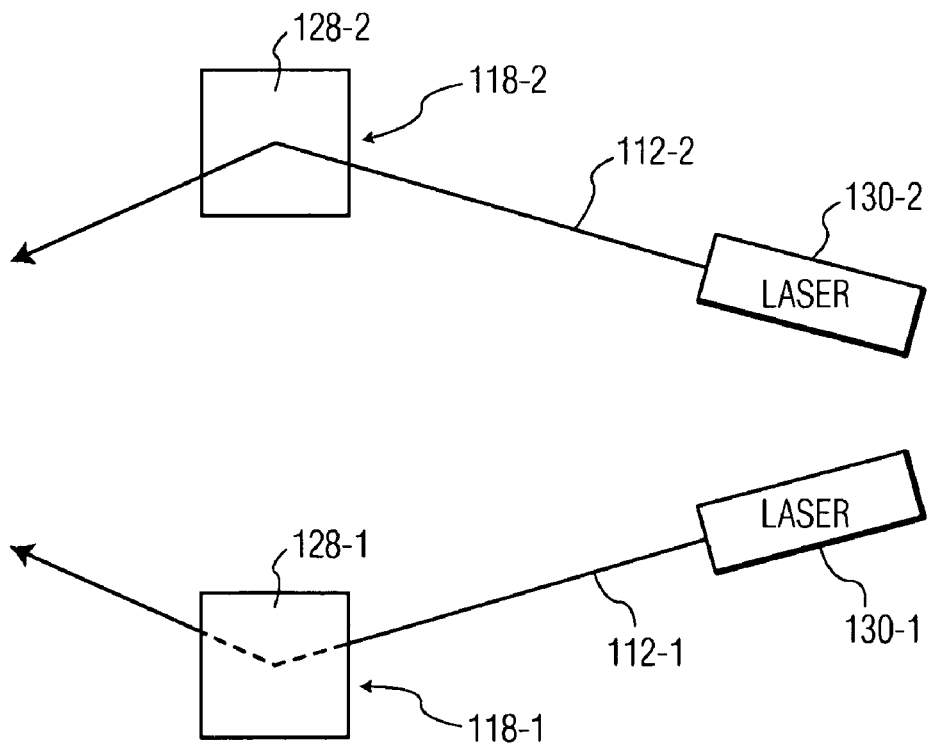

FIG. 5 is a simplified schematic diagram view illustrating an electro-magnetic tracking system featuring position optimization and a method thereof according to another embodiment of the present disclosure; and FIGS. 6-7 are schematic view diagrams of various apparatus used in connection with visibly optimizing a positioning and orientation of an electro-magnetic field generator of FIG. 5 according to alternate embodiments of the present disclosure.

In the figures, like reference numerals refer to like elements. In addition, it is to be noted that the figures may not be drawn to scale.

The embodiments of the present disclosure provide a method to continuously confirm the relationship between the field generator and the work area/probe location in an electro-magnetic tracking system application. In one embodiment, a laser beam originating from the field generator is positioned and oriented to extend through the centroid of the "sweet spot". Accordingly, the presence of the laser beam, positioned and oriented to extend through the centroid of the "sweet spot" would instantly reveal to a system user the angular alignment of the field generator to the work area.

Figure 1:
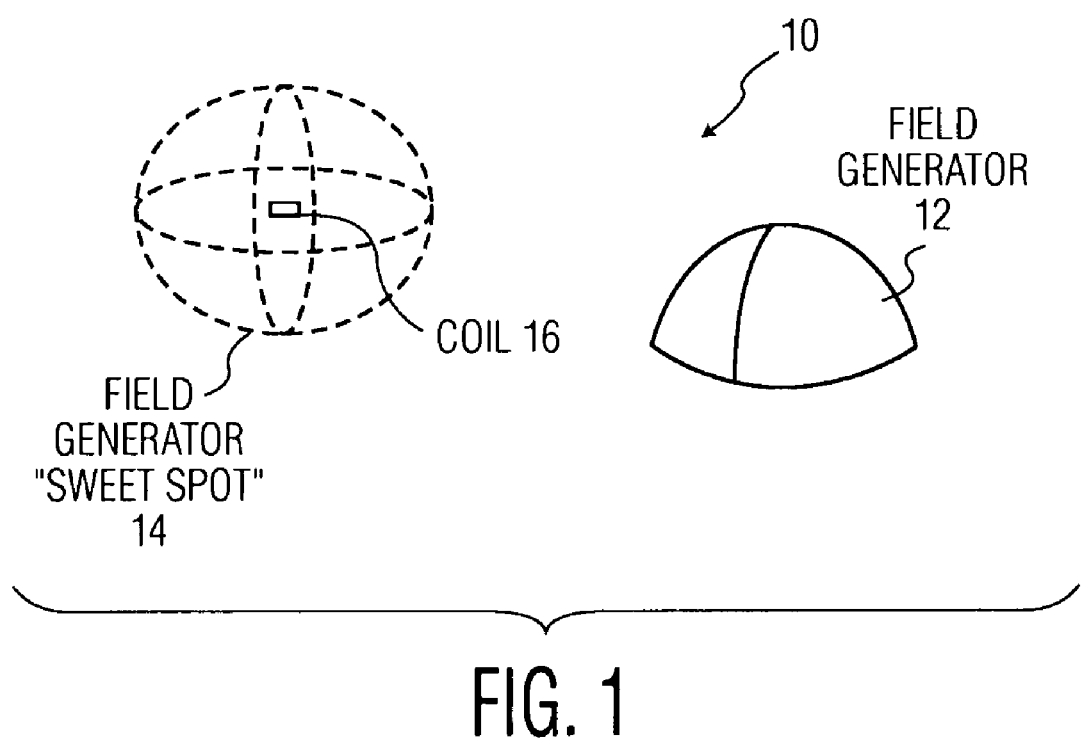
FIG. 1 is a diagram view of an electro-magnetic tracking system as known in the art.
Figure 2:
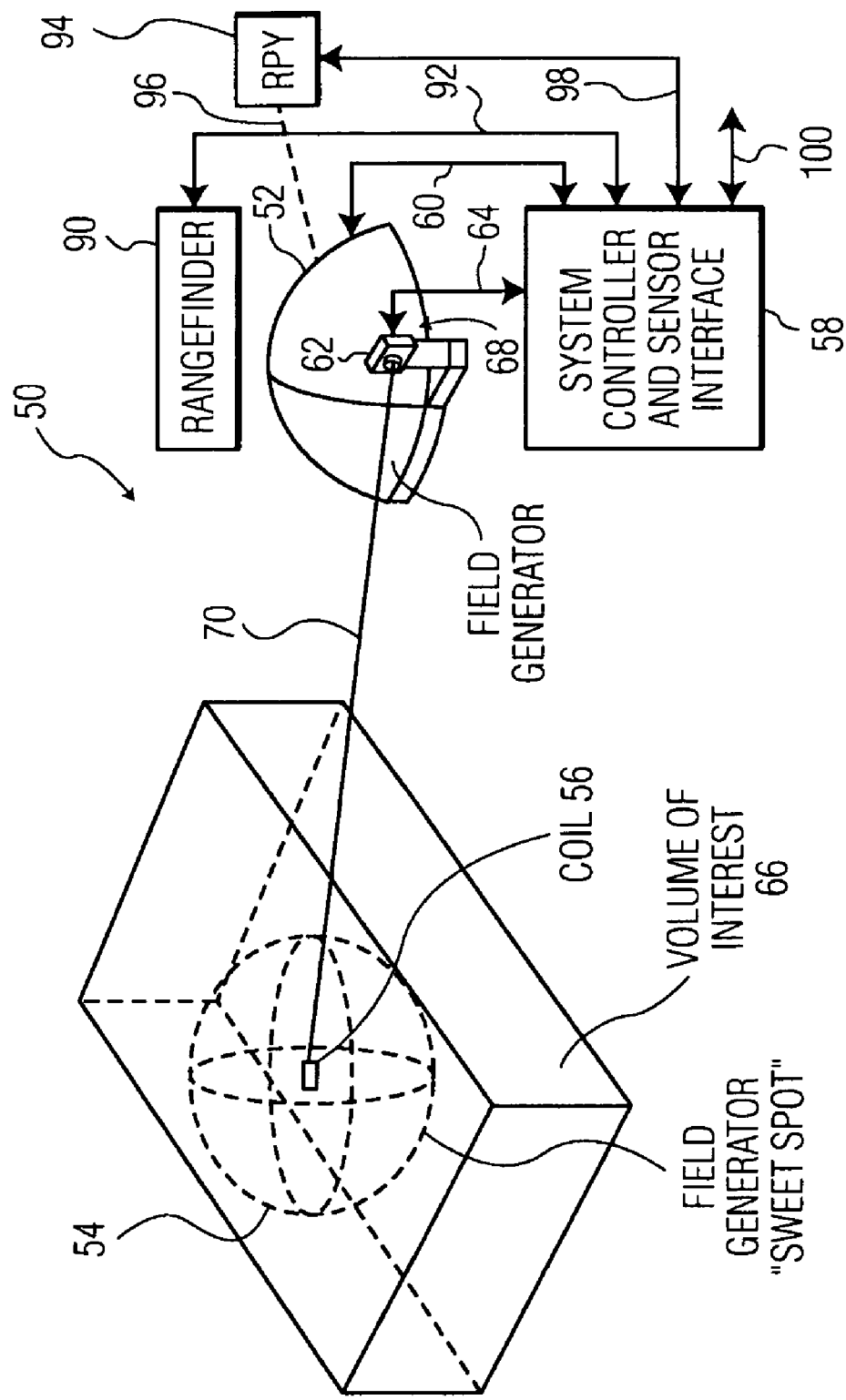
FIG. 2 is a simplified schematic diagram view illustrating an electro-magnetic tracking system featuring position optimization and a method thereof according to an embodiment of the present disclosure.

FIG. 2 is a simplified schematic diagram view illustrating an electro-magnetic tracking system 50 featuring position optimization and a method thereof according to an embodiment of the present disclosure. The electro-magnetic tracking system 50 includes an electro-magnetic field generator 52 which generates waves directed into a tracking volume. A preferred tracking volume that is characterized as having the highest accuracy is called the "sweet spot" of the electro-magnetic tracking system, indicated by reference numeral 54. A sensor coil 56 is illustrated as occurring within the sweet spot 54. The "ideal placement" of the electro-magnetic field generator is such that the sweet spot 54 lies in the centroid of the physical area to be probed with a tracked medical device or devices. The "ideal placement" may also be affected by the environment, in particular by any objects interfering with the electro-magnetic field of the tracking system.

The electro-magnetic tracking system 50 further includes a system controller 58 having a sensor interface. While the sensor interface is illustrated as being a portion of the system controller, the sensor interface could also be an individual unit separate from, but electronically coupled to the system controller. The electro-magnetic field generator 52 is responsive to the system controller 58, via suitable control signal(s) on signal line 60, for generating the electro-magnetic field. As mentioned, the electro-magnetic field includes a portion thereof characterized as a tracking volume of highest accuracy. The highest accuracy corresponds to an accuracy of the sensor interface and system controller 58 to detect a sensor 56 physically located within the tracking volume versus a lesser accuracy of the sensor interface and system controller to detect the sensor if the sensor is located outside of the tracking volume.

The electro-magnetic tracking system 50 further includes a means 62 mechanically coupled to the electro-magnetic field generator 52, and further electrically coupled to system controller via signal line 64 (or signal lines, as appropriate for a given tracking system implementation). Means 62 is configured for enabling visible optimization of one or both of (i) a positioning and (ii) an angular orientation of the electro-magnetic field generator 52 such that the tracking volume 54 substantially lies within a centroid of a physical volume of interest 66. Accordingly, such an embodiment enables detection of a sensor 56 within the tracking volume with a highest accuracy. The means 62 for visibly optimizing one or both of (i) a positioning and (ii) an angular orientation of the electro-magnetic field generator 52 further comprises component materials selected so as to not significantly degrade or distort the electro-magnetic field.

In one embodiment, means 62 for visibly optimizing the one or both of the positioning and the angular orientation of the electro-magnetic field generator 52 comprises a laser beam source. The laser beam source is mechanically coupled to the electro-magnetic field generator 52 at an origination point 68 proximate the electro-magnetic field generator in a predetermined position and orientation. In operation, responsive to a suitable activation signal from the system controller 58 via signal line(s) 64, the laser beam source projects a laser beam 70 that intersects a center of the tracking volume 54, whereby an angular alignment of the electro-magnetic field generator 52 to the physical volume of interest 66 can be adjusted and visibly verified via the laser beam so that the center of the tracking volume 54 can be angularly aligned with the centroid of the physical volume of interest 66. In one embodiment, the laser beam source comprises a semiconductor laser device.

Figure 3:
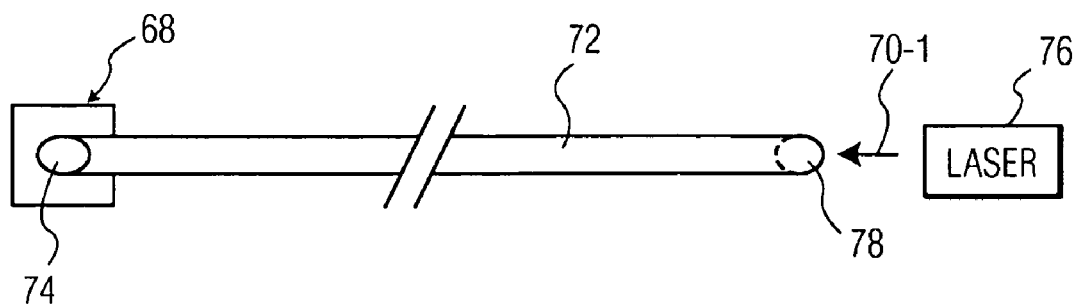
FIGS. 3 and 4 are schematic view diagrams of various apparatus used in connection with visibly optimizing a positioning and orientation of an electro-magnetic field generator of FIG. 2 according to alternate embodiments of the present disclosure.

In an alternate embodiment, as shown in FIG. 3, the laser beam source 62 of FIG. 2 comprises an optical fiber 72 having a first end thereof 74 terminating at the origination point 68, wherein the origination point corresponds to a location proximate the electro-magnetic field generator and with respect to a predetermined position and orientation. In such an embodiment, the system 50 further comprises a laser device 76 for producing the laser beam 70-1, wherein the laser beam is optically coupled into the optical fiber 72 at a second end 78 opposite the first end 74 thereof. Laser device 76 can be located remote from the field generator 52, according to the particular requirements of the electro-magnetic tracking system implementation.

Figure 4:
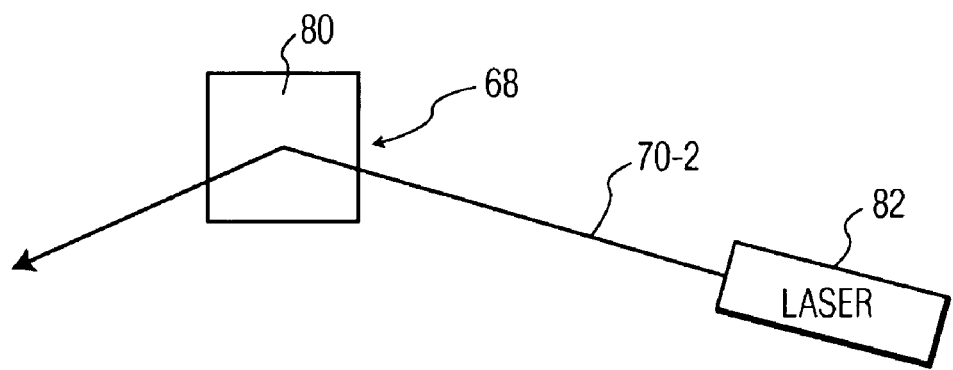

In another embodiment, as shown in FIG. 4, the laser beam source 62 of FIG. 2 comprises a mirror 80 located at the origination point, wherein the origination point corresponds to a location proximate the electro-magnetic field generator and with respect to a predetermined position and orientation.

In such an embodiment, the system 50 further comprises a laser device 82 for producing the laser beam 70-2, wherein the laser beam is directed into the mirror 80 and the mirror reflects the laser beam 70-2 such that the laser beam intersects the center of the tracking volume 54. Laser device 80 can be located remote from the field generator 52, according to the particular requirements of the electro-magnetic tracking system implementation.

Referring again to FIG. 2, in another embodiment, the electro-magnetic tracking system 50 further comprises a rangefinder 90. Rangefinder 90 can include, for example, any suitable rangefinder for determining a distance between a remote object (i.e., the volume of interest 66) and the electro-magnetic field generator 52 substantially along a line of sight of the laser beam 70. In one embodiment, the rangefinder 90 is coupled to system controller 58 for providing one or more of distance and/or control signal information there between, according to the requirements of a given tracking implementation. For example, rangefinder 90 may be coupled to the system controller 58 via signal line(s) 92. In operation, the rangefinder 90 provides a rangefinder output signal representative of the distance, whereby a positioning and orientation of the electro-magnetic field generator can be adjusted and visibly verified via the laser beam 70 and as a function of the rangefinder output signal so that the center of the tracking volume 54 substantially corresponds to the centroid of the physical volume of interest 66.

In one embodiment, the rangefinder output signal 92 comprises a numeric feedback signal. In another embodiment, the rangefinder output signal comprises an alarm, the alarm being indicative that the distance from the electro-magnetic field generator 52 to a remote object (e.g., the volume of interest 66) corresponds to a distance from the electro-magnetic field generator to a desired portion of the tracking volume 54. Furthermore, the desired portion of the tracking volume 54 may include one or more of (i) an outer perimeter of the tracking volume, (ii) a prescribed perimeter occurring within the tracking volume, and (iii) a center of the tracking volume.

In a further embodiment, the electro-magnetic tracking system 50 further comprises means 94 coupled (via mechanical or other suitable coupling as indicated by reference numeral 96) to the electro-magnetic field generator 52. Means 94 is configured for providing an output signal, for example, on signal line(s) 98, representative of an angular relationship of the tracking volume 54 of the electro-magnetic field generator to the physical volume of interest 66. The angular relationship includes one or more of roll, pitch, and yaw. In one embodiment, the angular relationship means 94 comprises a roll, pitch, and yaw sensor coupled to the electro-magnetic field generator 52. Still further, system controller 58 can include an input/output, generally indicated by reference numeral 100, wherein the input/output may be coupled to an input device or used for being coupled to one or more remote processing or computer system(s), for example, via an intranet, extranet, Internet, or other type of network.

Referring now to FIG. 5, in another embodiment of the present disclosure, the electromagnetic tracking system 110 comprises use of two or more laser beams separated at the point of origin (i.e., proximate the field generator 52) and convergent at a point in the center of the "sweet spot." In FIG. 5, only two laser beams (112-1, 112-2) are shown for simplicity of illustration. Such an embodiment would permit an extremely graphic and intuitive aid for a system user or operator.

The electro-magnetic tracking system 110 includes an electro-magnetic field generator 52 which generates waves directed into a tracking volume. A preferred tracking volume that is characterized as having the highest accuracy is called the "sweet spot" of the electro-magnetic tracking system, indicated by reference numeral 54. A sensor coil 56 is illustrated as occurring within the sweet spot 54. The "ideal placement" of the electro-magnetic field generator is such that the sweet spot 54 lies in the centroid of the physical area to be probed with a tracked medical device or devices. The "ideal placement" may also be affected by the environment, in particular by any objects interfering with the electro-magnetic field of the tracking system.

The electro-magnetic tracking system 110 further includes a system controller 58 having a sensor interface. While the sensor interface is illustrated as being a portion of the system controller, the sensor interface could also be an individual unit separate from, but electronically coupled to the system controller. The electro-magnetic field generator 52 is responsive to the system controller 58, via suitable control signal(s) on signal line 60, for generating the electro-magnetic field. As mentioned, the electro-magnetic field includes a portion thereof characterized as a tracking volume of highest accuracy. The highest accuracy corresponds to an accuracy of the sensor interface and system controller 58 to detect a sensor 56 physically located within the tracking volume versus a lesser accuracy of the sensor interface and system controller to detect the sensor if the sensor is located outside of the tracking volume.

The electro-magnetic tracking system 110 of FIG. 5 still further includes means 114 mechanically coupled to the electro-magnetic field generator 52, and further electrically coupled to system controller via signal line 116 (or signal lines, as appropriate for a given tracking system implementation). Means 114 is configured for enabling visible optimization of one or both of (i) a positioning and (ii) an angular orientation of the electro-magnetic field generator 52. In one embodiment, means 114 comprises first and second laser beam sources (114-1, 114-2) coupled to the electro-magnetic field generator 52 at respective first and second origination points (118-1, 118-2) in predetermined positions and orientations. Responsive to one or more activation signals from the system controller 58, the first and second laser beam sources (114-1, 114-2) project first and second laser beams (112-1, 112-2), respectively, that intersect at a center of the tracking volume 54, whereby a positioning and orientation of the electro-magnetic field generator 52 can be adjusted and visibly verified via the laser beams so that the center of the tracking volume 54 substantially corresponds to the centroid of the physical volume of interest 66.

In one embodiment, the first and second laser beam sources (114-1, 114-2) comprise first and second semiconductor laser devices. In another embodiment, as shown in FIG. 6, the first and second laser beam sources (114-1, 114-2) comprise first and second optical fibers (120-1, 120-2) each having first ends (122-1, 122-2) thereof terminating at the first and second origination points (118-1, 118-2), respectively. In such an embodiment, the system 110 further comprises at least one laser device (124-1, 124-2) for producing the first and second laser beams (112-1, 112-2), wherein the laser beams are optically coupled into the first and second optical fibers (120-1, 120-2), respectively, at second ends (126-1, 126-2) opposite the first ends thereof.

In another embodiment, as shown in FIG. 7, the first and second laser beam sources (114-1, 114-2) comprise first and second mirrors (128-1, 128-2) located at the first and second origination points (118-1, 118-2), respectively. In such an embodiment, the system 110 further comprises at least one laser device (130-1, 130-2) for producing the first and second laser beams (112-1, 112-2), wherein the laser beams are directed into the first and second mirrors (128-1, 128-2) and the first and second mirrors reflect the laser beams such that the laser beams intersect at the center of the tracking volume 54.

In yet another embodiment, the electro-magnetic field tracking system includes a range finder. The range finder can comprise, for example, a laser ranging (or other) system to provide numeric feedback about the distance of the electro-magnetic field generator from the target object. In a further embodiment, the electro-magnetic field tracking system includes a tool to provide information about the current angular relationship of the electro-magnetic field generator of the tracking system (i.e., roll, pitch, and yaw).

The embodiments disclosed herein can be implemented using suitable devices that are implemented and configured to operate in a manner as discussed herein. However, care must be taken in that the materials of the laser beam source and any associated wiring must not degrade or distort the field of the field generator. This is accomplished by choosing the components of the laser beam source and any associated wiring carefully. Alternatively, in one embodiment, small mirrors are mounted on the field generator and one or more laser beams are pointed to these mirrors, whereby the mirrors simulate the laser origin. Yet another way to avoid distortion of the generated electro-magnetic field is by using fiber-optics to deliver the laser source to the field generator. Alternately, a single laser ranging system could be employed. As a result, the embodiments of the present disclosure provide a continuous reference to a system user, reassuring correct orientation and allowing rapid repositioning if alignment is disturbed due to turbulent operating room conditions.

According to yet another embodiment of the present disclosure, an electro-magnetic tracking method comprises providing a system controller having a sensor interface; generating an electro-magnetic field with an electro-magnetic field generator in response to an activation signal of a system controller, the electro-magnetic field including a portion thereof characterized as a tracking volume of highest accuracy, wherein the highest accuracy corresponds to an accuracy of the sensor interface and system controller to detect a sensor physically located within the tracking volume versus a lesser accuracy of the sensor interface and system controller to detect the sensor if the sensor is located outside of the tracking volume; and optimizing one or both of (i) a positioning and (ii) an angular orientation of the electro-magnetic field generator, with use of a positioning and angular orientation visibility assistance member coupled to the electro-magnetic field generator, such that the tracking volume lies within a centroid of a physical volume of interest, thereby enabling a detection of a sensor within the tracking volume with a highest accuracy.

In one embodiment of the electro-magnetic tracking method, the positioning and the angular orientation visibility assistance member comprises one or more of (i) a laser beam source coupled to the electro-magnetic field generator at an origination point in a predetermined position and orientation, wherein responsive to an activation signal from the system controller, the laser beam source projects a laser beam that intersects a center of the tracking volume, whereby an angular alignment of the electro-magnetic field generator to the physical volume of interest can be adjusted and visibly verified via the laser beam so that the center of the tracking volume can be angularly aligned with the centroid of the physical volume of interest; and (ii) first and second laser beam sources coupled to the electro-magnetic field generator at respective first and second origination points in predetermined positions and orientations, wherein responsive to one or more activation signals from the system controller, the first and second laser beam sources project first and second laser beams, respectively, that intersect at a center of the tracking volume, whereby a positioning and orientation of the electro-magnetic field generator can be adjusted and visibly verified via the laser beams so that the center of the tracking volume corresponds to the centroid of the physical volume of interest.

In one embodiment, the laser beam source comprises one of (a) a semiconductor laser device, (b) an optical fiber having a first end thereof terminating at the origination point, or (c) a mirror located at the origination point, wherein for the optical fiber, the method further comprises using a laser device for producing the laser beam and optically coupling the laser beam into the optical fiber at a second end opposite the first end thereof, and wherein for the mirror, the method further comprises using a laser device for producing the laser beam and directing the laser beam into the mirror, wherein the mirror reflects the laser beam such that the laser beam intersects the center of the tracking volume.

In a further embodiment, the method further includes using a rangefinder for determining a distance between a remote object and the electro-magnetic field generator substantially along a line of sight of the laser beam, the rangefinder providing a rangefinder output signal representative of the distance, whereby a positioning and orientation of the electro-magnetic field generator can be adjusted and visibly verified via the laser beam and the rangefinder output signal so that the center of the tracking volume substantially corresponds to the centroid of the physical volume of interest. The rangefinder output signal can comprise one or more of (i) a numeric feedback signal or (ii) an alarm, wherein an activation of the alarm is indicative that the distance from the electro-magnetic field generator to the remote object corresponds to a distance from the electro-magnetic field generator to a desired portion of the tracking volume.

In another embodiment, the electro-magnetic tracking method includes using first and second laser beam sources that comprise one of (a) first and second semiconductor laser devices, (b) first and second optical fibers each having first ends thereof terminating at the first and second origination points, respectively, or (c) first and second mirrors located at the first and second origination points, wherein for first and second optical fibers, the method further comprises using at least one laser device for producing the first and second laser beams and optically coupling the laser beams into the first and second optical fibers, respectively, at second ends opposite the first ends thereof, and wherein for first and second mirrors located at the first and second origination points, respectively, the method further comprises using at least one laser device for producing the first and second laser beams and directing the first and second laser beams into the first and second mirrors, wherein the first and second mirrors reflect the laser beams such that the laser beams intersect at the center of the tracking volume.

The method further includes using a rangefinder for determining a distance between a remote object and the electro-magnetic field generator substantially along a line of sight of the laser beam, the rangefinder providing a rangefinder output signal representative of the distance, whereby a positioning and orientation of the electro-magnetic field generator can be adjusted and visibly verified via the laser beam and the rangefinder output signal so that the center of the tracking volume substantially corresponds to the centroid of the physical volume of interest. In one embodiment, the rangefinder output signal comprises one or more of (i) a numeric feedback signal or (ii) an alarm, wherein an activation of the alarm is indicative that the distance from the electro-magnetic field generator to the remote object corresponds to a distance from the electro-magnetic field generator to a desired portion of the tracking volume.

Although only a few exemplary embodiments have been described in detail above, those skilled in the art will readily appreciate that many modifications are possible in the exemplary embodiments without materially departing from the novel teachings and advantages of the embodiments of the present disclosure. Accordingly, all such modifications are intended to be included within the scope of the embodiments of the present disclosure as defined in the following claims. In the claims, means-plus-function clauses are intended to cover the structures described herein as performing the recited function and not only structural equivalents, but also equivalent structures.

In addition, any reference signs placed in parentheses in one or more claims shall not be construed as limiting the claims. The word "comprising" and "comprises," and the like, does not exclude the presence of elements or steps other than those listed in any claim or the specification as a whole. The singular reference of an element does not exclude the plural references of such elements and vice-versa. One or more of the embodiments may be implemented by means of hardware comprising several distinct elements, and/or by means of a suitably programmed computer. In a device claim enumerating several means, several of these means may be embodied by one and the same item of hardware. The mere fact that certain measures are recited in mutually different dependent claims does not indicate that a combination of these measures cannot be used to an advantage.

The invention claimed is:

1. An electro-magnetic tracking system comprising:
a system controller having a sensor interface;
a generator responsive to the system controller, for generating an electro-magnetic field, the electro-magnetic field including a portion thereof characterized as a tracking volume of highest accuracy, wherein the highest accuracy corresponds to an accuracy of the sensor interface and system controller to detect a sensor physically located within the tracking volume versus a lesser accuracy of the sensor interface and system controller to detect the sensor if the sensor is located outside of the tracking volume;
a device coupled to the electro-magnetic field generator for visibly optimizing one or both of (i) a positioning and (ii) an angular orientation of the electro-magnetic field generator such that the tracking volume lies within a centroid of a physical volume of interest, thereby enabling a detection of a sensor within the tracking volume with a highest accuracy; and
a rangefinder for determining a distance between a remote object and the electro-magnetic field generator, the rangefinder providing a rangefinder output signal representative of the distance, whereby a positioning and orientation of the electro-magnetic field generator can be adjusted and visibly verified via the rangefinder output signal so that the center of the tracking volume substantially corresponds to the centroid of the physical volume of interest.

2. The electro-magnetic tracking system of claim 1, wherein the device for visibly optimizing comprises component materials selected so as to not significantly degrade or distort the electro-magnetic field.

3. The electro-magnetic tracking system of claim 1, wherein the device for visibly optimizing the one or both of the positioning and the angular orientation of the electro-magnetic field generator comprises a laser beam source, the laser beam source being coupled to the electro-magnetic field generator at an origination point in a predetermined position and orientation, wherein responsive to an activation signal from the system controller, the laser beam source projects a laser beam that intersects a center of the tracking volume, whereby an angular alignment of the electro-magnetic field generator to the physical volume of interest can be adjusted and visibly verified via the laser beam so that the center of the tracking volume can be angularly aligned with the centroid of the physical volume of interest.

4. The electro-magnetic tracking system of claim 3, further wherein the laser beam source comprises a semiconductor laser device.

5. The electro-magnetic tracking system of claim 3, further wherein the laser beam source comprises an optical fiber having a first end thereof terminating at the origination point, the system further comprising:
   a laser device for producing the laser beam, wherein the laser beam is optically coupled into the optical fiber at a second end opposite the first end thereof.

6. The electro-magnetic tracking system of claim 3, further wherein the laser beam source comprises a mirror located at the origination point, the system further comprising:
   a laser device for producing the laser beam, wherein the laser beam is directed into the mirror and the mirror reflects the laser beam such that the laser beam intersects the center of the tracking volume.

7. The electro-magnetic tracking system of claim 3, wherein the rangefinder is configured for determining a distance between a remote object and the electro-magnetic field generator substantially along a line of sight of the laser beam, and wherein the positioning and orientation of the electro-magnetic field generator can be adjusted and visibly verified via the laser beam and the rangefinder output signal so that the center of the tracking volume substantially corresponds to the centroid of the physical volume of interest.

8. The electro-magnetic tracking system of claim 7, wherein the rangefinder output signal comprises a numeric feedback signal.

9. The electro-magnetic tracking system of claim 7, wherein the rangefinder output signal comprises an alarm, the alarm being indicative that the distance from the electro-magnetic field generator to the remote object corresponds to a distance from the electro-magnetic field generator to a desired portion of the tracking volume.

10. The electro-magnetic tracking system of claim 9, further wherein the desired portion of the tracking volume includes one or more of (i) an outer perimeter of the tracking volume, (ii) a prescribed perimeter occurring within the tracking volume, and (iii) a center of the tracking volume.

11. The electro-magnetic tracking system of claim 1, wherein the for visibly optimizing a positioning and orientation of the electro-magnetic field generator comprises first and second laser beam sources coupled to the electro-magnetic field generator at respective first and second origination points in predetermined positions and orientations, wherein responsive to one or more activation signals from the system controller, the first and second laser beam sources project first and second laser beams, respectively, that intersect at a center of the tracking volume, whereby a positioning and orientation of the electro-magnetic field generator can be adjusted and visibly verified via the laser beams so that the center of the tracking volume corresponds to the centroid of the physical volume of interest.

12. The electro-magnetic tracking system of claim 11, wherein the first and second laser beam sources comprise first and second semiconductor laser devices.

13. The electro-magnetic tracking system of claim 11, wherein the first and second laser beam sources comprise first and second optical fibers each having first ends thereof terminating at the first and second origination points, respectively, the system further comprising:
   at least one laser device for producing the first and second laser beams, wherein the laser beams are optically coupled into the first and second optical fibers, respectively, at second ends opposite the first ends thereof.

14. The electro-magnetic tracking system of claim 11, further wherein the first and second laser beam sources comprise first and second mirrors located at the first and second origination points, respectively, the system further comprising:
   at least one laser device for producing the first and second laser beams, wherein the laser beams are directed into the first and second mirrors and the first and second mirrors reflect the laser beams such that the laser beams intersect at the center of the tracking volume.

15. An electro-magnetic tracking system comprising:
   a system controller having a sensor interface;
   a generator responsive to the system controller, for generating an electro-magnetic field, the electro-magnetic field including a portion thereof characterized as a tracking volume of highest accuracy, wherein the highest accuracy corresponds to an accuracy of the sensor interface and system controller to detect a sensor physically located within the tracking volume versus a lesser accuracy of the sensor interface and system controller to detect the sensor if the sensor is located outside of the tracking volume;
   a device coupled to the electro-magnetic field generator for visibly optimizing one or both of (i) a positioning and (ii) an angular orientation of the electro-magnetic field generator such that the tracking volume lies within a centroid of a physical volume of interest, thereby enabling a detection of a sensor within the tracking volume with a highest accuracy; and
   an angular relationship device coupled to the electro-magnetic field generator for providing an output signal representative of an angular relationship of the tracking volume of the electro-magnetic field generator to the physical volume of interest, wherein the angular relationship includes one or more of roll, pitch, and yaw.

16. The electro-magnetic tracking system of claim 15, wherein said angular relationship device comprises a roll, pitch, and yaw sensor coupled to the electro-magnetic field generator.

17. An electro-magnetic tracking method comprising the acts of:
   providing a system controller having a sensor interface;
   generating an electro-magnetic field with an electro-magnetic field generator in response to an activation signal of a system controller, the electro-magnetic field including a portion thereof characterized as a tracking volume of highest accuracy, wherein the highest accuracy corresponds to an accuracy of the sensor interface and system controller to detect a sensor physically located within the tracking volume versus a lesser accuracy of the sensor interface and system controller to detect the sensor if the sensor is located outside of the tracking volume;
   optimizing one or both of (i) a positioning and (ii) an angular orientation of the electro-magnetic field generator, with use of a positioning and angular orientation visibility assistance member coupled to the electro-magnetic field generator, such that the tracking volume lies within a centroid of a physical volume of interest, thereby enabling a detection of a sensor within the tracking volume with a highest accuracy; and using a rangefinder for determining a distance between a remote object and the electro-magnetic field generator, the rangefinder providing a rangefinder output signal representative of the distance, whereby a positioning and orientation of the electro-magnetic field generator can be adjusted and visibly verified via the rangefinder output signal so that the center of the tracking volume substantially corresponds to the centroid of the physical volume of interest.

18. The method of claim 17, wherein the positioning and the angular orientation visibility assistance member comprises one or more of:

(i) a laser beam source coupled to the electro-magnetic field generator at an origination point in a predetermined position and orientation, wherein responsive to an activation signal from the system controller, the laser beam source projects a laser beam that intersects a center of the tracking volume, whereby an angular alignment of the electro-magnetic field generator to the physical volume of interest can be adjusted and visibly verified via the laser beam so that the center of the tracking volume can be angularly aligned with the centroid of the physical volume of interest; and (ii) first and second laser beam sources coupled to the electro-magnetic field generator at respective first and second origination points in predetermined positions and orientations, wherein responsive to one or more activation signals from the system controller, the first and second laser beam sources project first and second laser beams, respectively, that intersect at a center of the tracking volume, whereby a positioning and orientation of the electro-magnetic field generator can be adjusted and visibly verified via the laser beams so that the center of the tracking volume corresponds to the centroid of the physical volume of interest.

19. The method of claim 18, further wherein the laser beam source comprises one of (a) a semiconductor laser device, (b) an optical fiber having a first end thereof terminating at the origination point, or (c) a mirror located at the origination point, wherein for the optical fiber, the method further comprises using a laser device for producing the laser beam and optically coupling the laser beam into the optical fiber at a second end opposite the first end thereof, and wherein for the mirror, the method further comprises using a laser device for producing the laser beam and directing the laser beam into the mirror, wherein the mirror reflects the laser beam such that the laser beam intersects the center of the tracking volume.

20. The method of claim 19, wherein the rangefinder determines the distance between the remote object and the electro-magnetic field generator substantially along a line of sight of the laser beam, and wherein the positioning and orientation of the electro-magnetic field generator can be adjusted and visibly verified via the laser beam and the rangefinder output signal so that the center of the tracking volume substantially corresponds to the centroid of the physical volume of interest.

21. The method of claim 20, wherein the rangefinder output signal comprises one or more of (i) a numeric feedback signal or (ii) an alarm, wherein an activation of the alarm is indicative that the distance from the electro-magnetic field generator to the remote object corresponds to a distance from the electro-magnetic field generator to a desired portion of the tracking volume.

22. An electro-magnetic tracking method comprising:

providing a system controller having a sensor interface;

generating an electro-magnetic field with an electro-magnetic field generator in response to an activation signal of a system controller, the electro-magnetic field including a portion thereof characterized as a tracking volume of highest accuracy, wherein the highest accuracy corresponds to an accuracy of the sensor interface and system controller to detect a sensor physically located within the tracking volume versus a lesser accuracy of the sensor interface and system controller to detect the sensor if the sensor is located outside of the tracking volume; and optimizing one or both of (i) a positioning and (ii) an angular orientation of the electro-magnetic field generator, with use of a positioning and angular orientation visibility assistance member coupled to the electro-magnetic field generator, such that the tracking volume lies within a centroid of a physical volume of interest, thereby enabling a detection of a sensor within the tracking volume with a highest accuracy;

wherein the positioning and the angular orientation visibility assistance member comprises first and second laser beam sources coupled to the electro-magnetic field generator at respective first and second origination points in predetermined positions and orientations, wherein responsive to one or more activation signals from the system controller, the first and second laser beam sources project first and second laser beams, respectively, that intersect at a center of the tracking volume, whereby a positioning and orientation of the electro-magnetic field generator can be adjusted and visibly verified via the laser beams so that the center of the tracking volume corresponds to the centroid of the physical volume of interest, wherein the first and second laser beam sources comprise one of (a) first and second semiconductor laser devices, (b) first and second optical fibers each having first ends thereof terminating at the first and second origination points, respectively, or (c) first and second mirrors located at the first and second origination points, wherein for first and second optical fibers, the method further comprises using at least one laser device for producing the first and second laser beams and optically coupling the laser beams into the first and second optical fibers, respectively, at second ends opposite the first ends thereof, and wherein for first and second mirrors located at the first and second origination points, respectively, the method further comprises using at least one laser device for producing the first and second laser beams and directing the first and second laser beams into the first and second mirrors, wherein the first and second mirrors reflect the laser beams such that the laser beams intersect at the center of the tracking volume.

23. The method of claim 22, further comprising:

using a rangefinder for determining a distance between a remote object and the electro-magnetic field generator substantially along a line of sight of the laser beam, the rangefinder providing a rangefinder output signal representative of the distance, whereby a positioning and orientation of the electro-magnetic field generator can be adjusted and visibly verified via the laser beam and the rangefinder output signal so that the center of the tracking volume substantially corresponds to the centroid of the physical volume of interest.

24. The method of claim 23, wherein the rangefinder output signal comprises one or more of (i) a numeric feedback signal or (ii) an alarm, wherein an activation of the alarm is indicative that the distance from the electro-magnetic field generator to the remote object corresponds to a distance from the electro-magnetic field generator to a desired portion of the tracking volume.

* * * * *